United States Patent [19]

Kurtz et al.

[11] 4,015,603
[45] Apr. 5, 1977

[54] SURGICAL DRAINAGE SYSTEM WITH PRESSURE INDICATOR

[75] Inventors: Leonard D. Kurtz, Woodmere; Robert E. Bidwell, Melville, both of N.Y.

[73] Assignee: Deknatel Inc., Queens Village, N.Y.

[22] Filed: Oct. 10, 1975

[21] Appl. No.: 621,600

[52] U.S. Cl. ............................................... 128/276
[51] Int. Cl.² ........................................ A61M 1/00
[58] Field of Search ......................... 128/275–278, 128/294–295, 2 F, DIG. 24, DIG. 29, 348–350 V, 299–300, 2.05 D; 137/176, 525.1, 205, 271; 141/59, 35, 7, 59; 73/200, 401, 299, 302, 303

[56] References Cited
UNITED STATES PATENTS

| | | |
|---|---|---|
| 2,936,757 | 5/1960 | Trace .............................. 128/276 |
| 3,730,168 | 5/1973 | McWhorter .................. 128/2.05 D |
| 3,783,870 | 1/1974 | Schachet ........................... 128/276 |
| 3,847,152 | 11/1974 | Schachet ........................... 128/276 |

Primary Examiner—J. Reed Fisher
Attorney, Agent, or Firm—Larson, Taylor & Hinds

[57] ABSTRACT

A surgical drainage system is provided for the drainage of fluid from a body cavity which comprises a first collection compartment, a second compartment, and a connecting passageway for connecting the first and second compartment in fluid communication. The volume of the connecting passageway is insignificant with respect to the second compartment and the connecting passageway provides a visual indication of changes in pressure in the body cavity by reason of oscillation of collected fluid therein.

5 Claims, 2 Drawing Figures

SURGICAL DRAINAGE SYSTEM WITH PRESSURE INDICATOR

BACKGROUND OF THE INVENTION

1. Field of the Invention

This invention relates to surgical drainage systems and more particularly to apparatus for draining fluids from a body cavity.

2. Description of the Prior Art

In order for a person to maintain a normal breathing pattern, his pleural cavity must be relatively free of fluids. These fluids, which may be generated in the cavity following, for example, lung surgery, foreign objects piercing the rib cage, or pleurisy, obstruct normal pressure changes in the cavity, thereby interfering with breathing.

Many techniques have been employed to remove this fluid. One method for removing excess fluids is by means of drainage systems such as shown in Bidwell et al. U.S. Pat. Nos. 3,363,626 and 3,363,627. As pointed out in above mentioned patents, the treatment for such pleural cavity imbalance is generally known as "underwater drainage" and involves the removal of fluids from the cavity into a collection chamber and which may include a suction system to maintain any desired degree of negativity in the pleural cavity.

An examination of prior art systems will reveal that there is a need for a drainage system which is not bulky, and which can be set up under emergency conditions without the need to fill the various underwater seal chambers, incorporated therein for pressure regulation purposes, with sterile fluid. Further there is a need for a simple, inexpensive system made of transparent material incorporating means for indicating and monitoring changing pressure conditions in the pleural cavity, so as to enable a clinician with minimal training, to quickly determine pressure changes within the pleural cavity. Standard pressure indication means as now provided in underwater drainage devices give a general indication of pressure conditions in the pleural cavity but are not capable of giving a precise indication of pressure fluctuations within the pleural cavity.

Also in an emergency situation when a patient may be very weak or when dealing with infants that have small pleural cavities, it is important that the additional space in the underwater drainage apparatus, referred to as "dead air space", be reduced as much as possible so as not to tax the already limited energies of the patient in breathing. Most prior art underwater drainage devices expose the patient's pleural cavity directly to a large collection cavity. Thus the patients breathing system must effect pressure variations both of both its own cavity as well as the collection chamber of the drainage apparatus in order to breathe.

Finally as with all drainage systems there is a continuing need for a system which can be placed in an antiseptic state.

SUMMARY OF THE INVENTION

The present invention provides for a surgical drainage system that overcomes the disadvantages associated with the prior art devices noted hereinbefore. There is provided a pressure fluctuation indication means that can instantaneously indicate the rate of pressure fluctuation within the pleural cavity. This system is simple and may be made operable, especially in emergency situations, with only minimal preparation. Further, this invention combines therewith an underwater seal that enables the dead air space which is connected with the pleural cavity by the underwater drainage device to be reduced drastically. Finally this invention is of simple construction, inexpensive and easily placed in an antiseptic state.

In accordance with a preferred embodiment of the invention, a surgical drainage system for the drainage of a cavity is provided which comprises a first collection compartment in communication with the cavity to be drained and a second chamber adjacent thereto. The first and second chambers are placed in fluid communication by a connecting passageway, the volume of which is insignificant with respect to the second compartment. The connecting passageway further provides for visual indication of any oscillation of fluid therein caused by changes in pressure in the pleural cavity.

Additional features and advantages of the invention will be set forth in, or apparent from, the detailed description of the preferred embodiments of the invention found hereinbelow.

DETAILED DESCRIPTION OF THE PREFERRED EMBODIMENTS

Figure 2:
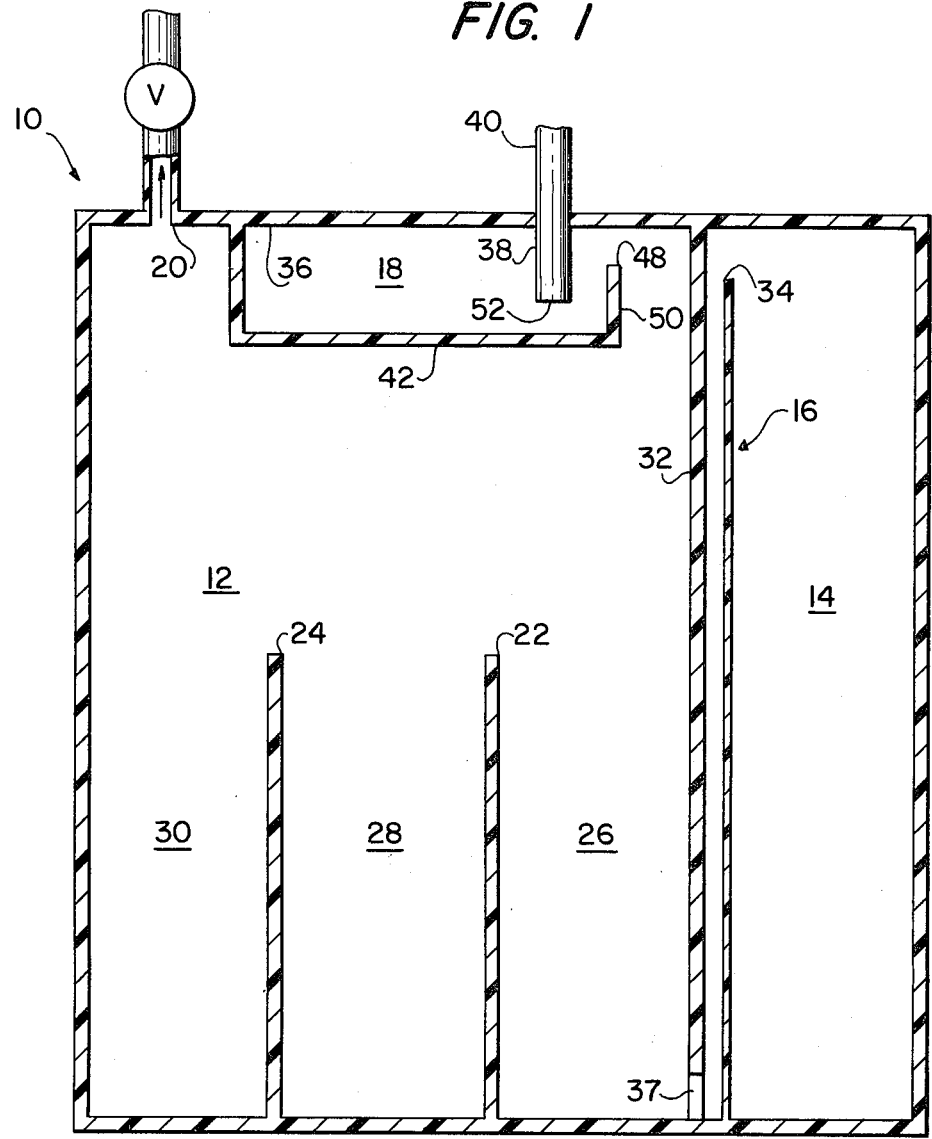
FIG. 2 is a cross-sectional, side elevation view taken along line 2—2 of FIG. 1.

With reference to the Figures and, in particular, to FIG. 2, there is disclosed the preferred embodiment of surgical drainage system 10. For purposes of description, surgical drainage system 10 can be broken into the following functional units: a collecting compartment 12, a second adjacent compartment 14, a passageway 16 connecting the two compartments, an underwater seal chamber 18 that connects the body cavity to the collection chamber 12, and an aperture 20 that connects the collection chamber 12 to a source of vacuum (not shown).

The collection chamber 12 is the chamber for receiving the fluid drained from a body cavity. As shown in FIG. 2, the lower half of rectangularly shaped compartment 12 is partitioned by baffles 22 and 24 into three smaller chambers 26, 28 and 30. Drained fluid fills the smaller chambers sequentially starting with chamber 26, excess fluid then overflowing into chamber 28 and so on until all three chambers are filled. It should be noted since compartment 12, as well as the entire system 10, is comprised of a transparent material, the amount of fluid in collection chamber 12 can be quickly determined by observing the filled state of these smaller chambers 26, 28 and 30. Further, scales may be applied to the external surface of these chambers 26, 28 and 30 to facilitate determination of the fluid content of the collection chamber. It should be noted that the number and size of these smaller chambers may be changed so as to accommodate various rates and amounts of drained fluid and so as to better indicate these amounts and rates to an observer.

The compartment 14 is similarly rectangularly shaped as can be seen in the cross-sectional view depicted in FIG. 2. Compartment 14 shares a common wall 32 with compartment 12. Compartment 14 can alternatively be referred to as a blind chamber since it has only one aperture 34 to provide communication with collection chamber 12.

Figure 1:
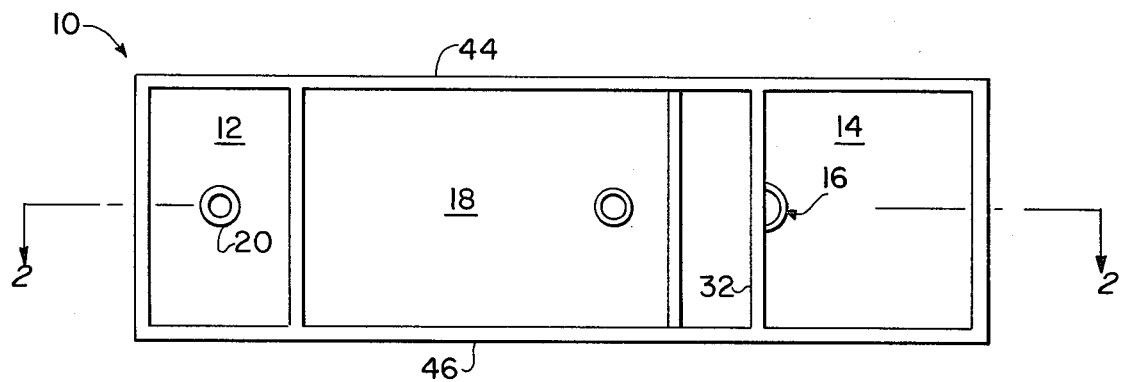
FIG. 1 is a plan view of the surgical drainage system in accordance with the invention.

The passageway 16, that connects the top of compartment 14 through aperture 34 to the bottom of chamber 12 through aperture 37, is formed by an elongated tube, semicircular in cross-section as shown in FIG. 1. Passageway 16 has a volume which is insignificant in comparison to the volume of compartment 14. When fluid enters passageway 16, compartment 14 is effectively closed off from compartment 12. Consequently, because of this sealing effect and because passageway 16 has an insignificant volume in comparison to compartment 14, compartment 14 maintains a constant pressure regardless of the fluid fluctuations in passageway 16.

Located inside collection compartment 12 and generally affixed to the upper wall 36 thereof, is the underwater seal chamber 18. There is provided an aperture 38 in wall 36 through which a thoracotomy tube 40 is force fitted. A cup member 42 is affixed to side walls 44 and 46 and to top wall 36 of the collection chamber 12. A connecting opening 48 from cup member 42 to compartment 12 is formed above the upper end of wall 50 of cup member 42. Opening 48 is directly above chamber 26. Fluid drains from the body cavity through thoracotomy tube 40. Tube 40 projects far enough into cup member 42 so that fluid, as it fills member 42, covers end 52 of tube 40 before it flows through opening 48 into chamber 26 of compartment 12. Also it should be noted that a check valve such as that described in the Bidwell U.S. Pat. No. 3,809,085 can be placed in tube 40 between system 10 and the pleural cavity so as to prevent the flow of fluid back into the pleural cavity.

The collection chamber 12 has an aperture 20 located in wall 36 above chamber 30. Aperture 20 is connected to a source of vacuum through regulator V. The vacuum source and regulator V are of standard designs. (Also a one way flap valve can be inserted between regulator V and aperture 20 which closes, if for some reason, the vacuum source fails.) System 10 can be constructed of any tough, rigid, impact-resistant, transparent plastic capable of being antiseptically cleaned. Further, system 10 can be of one piece construction using a method of manufacture such as, for example, blow molding, pressure forming, injection molding or slush molding. In the alternative, however, the elements of system 10 may be individually manufactured and connected into an integral unit.

In operation of drainage system 10, one end of tube 40 is placed in the body cavity to be drained. The vacuum source is switched on and regulator V is set. The setting of regulator V is such that the proper vacuum is maintained in the pleural body cavity while fluid is drained therefrom so that the normal breathing pattern will not be interrupted.

Fluid flows through tube 40 and into the seal chamber 18. Fluid fills seal 18, so that the tube end 52 is completely submerged thereby, until the fluid overflows the seal chamber 18 and pours into chamber 26 of collection compartment 12.

By locating the seal immediately adjacent the end of the thoracotomy tube 40, the volume of the collection chamber is eliminated from that space which the patient must pressure regulate by his breathing. In most conventional underwater drainage devices the seal is located so that the volume of the collection chamber is included in the volume which the patient must regulate to breathe normally. This places an additional workload on the patient's breathing mechanism at the very time when the patient could least afford it. Thus in the case of an adult patient, seal 18 allows the patient to breathe more easily. Further, seal 18 is vitally essential when system 10 is used on an infant patient, since an infant's pleural cavity is much smaller than one of an adult and thus the additional dead air space of the collection chamber would have a more damaging effect on an infant's breathing function.

If regulator V malfunctions and system 10 is exposed to atmospheric pressure, seal 18 prevents the pleural cavity from being exposed to this pressure and thus prevents lung collapse.

As the fluid overflows seal 18 and fills chamber 26, fluid flows through aperture 36 into passageway 16. Once fluid has filled chamber 26 to a level above aperture 37, second compartment 14 becomes sealed off from the rest of system 10. Since the volume of passageway 16 is insignificant in comparison to compartment 14, the flow of fluid into or out of passageway 16 does not change the pressure in compartment 14. Any oscillations of fluid in passageway 16 are not affected by back pressure in compartment 14. Since changes in pressure in the pleural cavity cause the fluid in passageway 16 to oscillate and since 14 does not influence these oscillations, these pressure changes can be easily and quickly monitored by visually observing these oscillations within passageway 16.

As fluid fills chamber 26, the amount of fluid can be visually observed and scales can be provided on wall 46 of system 10 to provide an accurate determination of the amount of fluid being drained from the patient.

When chamber 26 becomes filled it overflows into chamber 28 and chamber 28, when filled, in turn overflows into chamber 30. Once chambers 26, 28 and 30 have been filled, the remaining upper portion of first compartment 12 is used to contain further amounts of drained fluid.

Although the present invention has been described relative to an examplary embodiment thereof, it will be understood by those skilled in the art that variations and modifications can be effected in these embodiments without departing from the scope and spirit of the invention.

I claim:

1. A surgical drainage system adapted to receive a drainage tube for the drainage of a body cavity comprising a unitary, integral structure including:
   a first, gas-tight, collection compartment in fluid communication with the body cavity to be drained, said first compartment partitioned into a plurality of chambers, said collection compartment having a first port through the uppermost end of said compartment, said port adapted to receive the drainage tube so that the drainage tube extends downwardly through said port into said first compartment a distance substantially less than the height of said first compartment, said first compartment having a second port through the uppermost end of said compartment for placing said compartment in fluid communication with a source of vacuum;
   an underwater seal means for forming a fluid seal at the end of the drainage tube, said seal means including a second fluid collection compartment contained within said first compartment and having a volume that is small with respect to the volume of said first compartment, said second fluid collection compartment dependent downwardly from the uppermost portion of said first compartment, the drainage tube extending into said second compartment, said second compartment having a port in fluid communication with said first compartment, said port located above the fluid seal formed in said second compartment;

a third compartment located adjacent to and having a common wall with said first collection compartment; and a connecting passageway for connecting in fluid communication said first collection compartment and said third compartment, an opening in the lower end of said common wall between said first and third compartments in communication with the lower end of said connecting passageway, said connecting passageway being open at the upper end in communication with said third compartment so that the initial fluid drained from said port of said underwater seal means enters said first collection chamber so as to seal off said opening in said common wall and simultaneously seal off said third compartment and connecting passageway from said first compartment, the volume of said connecting passageway being small with respect to said third compartment, said connecting passageway providing visual indication of any oscillations of fluid therein caused by changes in pressure in the body cavity.

2. A surgical drainage system in accordance with claim 1 wherein the volume of said connecting passageway is at least a factor of 10 smaller than the volume of said third compartment.

3. A surgical drainage system in accordance with claim 1 wherein said system is comprised of a molded structure.

4. A surgical drainage system in accordance with claim 1 wherein said structure is comprised of a clear plastic material capable of being sterilized.

5. A surgical drainage system in accordance with claim 1 wherein said system is comprised of a rigid, impact resistant structure.

* * * * *